United States Patent [19]
Gilbert et al.

[11] Patent Number: 5,723,603
[45] Date of Patent: Mar. 3, 1998

[54] PROCESS FOR THE PREPARATION OF LACTAMS

[75] Inventors: Laurent Gilbert, Paris; Nathalie Laurain, Lyons; Philippe Leconte, Meyzieu; Christophe Nedez, Asnieres sur Seine, all of France

[73] Assignee: R.P. Fiber & Resin Intermediates, Courbevoie Cedex, France

[21] Appl. No.: 665,520

[22] Filed: Jun. 17, 1996

[30] Foreign Application Priority Data

Jun. 16, 1995 [FR] France ................... 95 07446

[51] Int. Cl.$^6$ .................. C07D 201/08; C07D 223/10
[52] U.S. Cl. ................. 540/539; 558/453; 564/490
[58] Field of Search ............... 564/490; 540/539; 558/453

[56] References Cited

U.S. PATENT DOCUMENTS

| | | | |
|---|---|---|---|
| 4,625,023 | 11/1986 | Mares et al. | 540/539 |
| 4,628,085 | 12/1986 | Mares et al. | 540/539 |
| 5,153,351 | 10/1992 | Sieja | 558/452 |
| 5,162,567 | 11/1992 | Sieja | 558/452 |
| 5,192,399 | 3/1993 | Sieja | 203/36 |

FOREIGN PATENT DOCUMENTS

| | | |
|---|---|---|
| 0150295 | 8/1985 | European Pat. Off. |
| 2029540 | 10/1970 | France |
| 4319134 | 12/1994 | Germany |
| 4339648 | 5/1995 | Germany |
| 93/14064 | 7/1993 | WIPO |
| 9316034 | 8/1993 | WIPO |
| 93/16984 | 9/1993 | WIPO |

OTHER PUBLICATIONS

Richard J. Lewis, Sr., *Hawley's Condensed Chemical Dictionary*, Twelfth Edition, 1993, pp. 679 and 823.

*Primary Examiner*—Mukund J. Shah
*Assistant Examiner*—Pavanaram K. Sripada
*Attorney, Agent, or Firm*—Burns, Doane, Swecker & Mathis, L.L.P.

[57] ABSTRACT

The present invention relates to a process for the preparation of lactams from dinitriles.

It consists more precisely of a process for the preparation of lactam, linking two stages in series, one of hemihydrogenation of dinitrile to aminonitrile, the other of cyclizing hydrolysis of the aminonitrile after only one simple purification operation.

Aliphatic lactams, such as especially epsilon-caprolactam, are base compounds for the preparation of polyamides (polyamide 6 from caprolactam).

31 Claims, No Drawings

PROCESS FOR THE PREPARATION OF LACTAMS

The present invention relates to a process for the preparation of lactams from dinitriles.

Aliphatic lactams such as especially epsilon-caprolactam are starting compounds for the preparation of polyamides (polyamide 6 from caprolactam).

On an industrial scale caprolactam is prepared from cyclohexanone, which is converted into its oxime. The oxime is then converted into caprolactam in the presence of a strong acid such as sulphuric acid, the excess of which must subsequently be neutralized. Such a process has the major disadvantage of giving rise to very large quantities of ammonium sulphate, up to several tons per ton of caprolactam prepared.

Another envisaged means for preparing these lactams consists in performing a partial hydrogenation of dinitriles to corresponding aminonitriles, more particularly of adiponitrile to aminocapronitrile, and in then carefully purifying the aminonitrile in order to remove all the impurities such as various imines or amines formed during the hydrogenation or else the diamine and, finally, in polymerizing the aminonitrile thus purified to polyamide.

This last process, which at first sight looks tempting, makes a very thorough purification of the aminonitrile absolutely necessary. In fact, the polymerization can be envisaged only if the aminonitrile is free from diamine and, above all, of the various imine or amine by-products which limit the degree of polymerization and cause the appearance of colouring and branching. However, the close similarity of the properties of the aminonitrile and of the imines or amines to be removed and, above all, the existence of equilibria between various forms of by-products are such that the separation is not easy and that it is necessary to add one or more compounds intended to convert the imines before removing them. Thus, Patent WO-A-9316984 proposes to add to the mixture to be treated up to 10% by weight of a carbonyl compound such as an aldehyde or a ketone. Patent WO-A-9314064 teaches introducing a methylene compound such as malononitrile, dicyclopentadiene, cyclopentadiene, nitromethane, nitroethane or indene to the reaction mixture before distilling it. This addition of compounds to a mixture which is already complex is not apt to simplify the process.

The present invention consists of a process for the preparation of lactam, linking two stages in series, one of hemihydrogenation of dinitrile to aminonitrile, the other of cyclizing hydrolysis of the aminonitrile after only one simple purification operation.

More precisely the invention consists of a process for the preparation of lactam, characterized in that:

an aliphatic dinitrile is hydrogenated to aminonitrile with hydrogen and in the presence of a catalyst, the aminonitrile obtained is distilled in order to have a dinitrile content lower than or equal to 10% by weight and a content of by-products containing an imine or amine functional group lower than or equal to 10% by weight, the distilled aminonitrile is reacted in vapour phase with water in the presence or absence of a catalyst.

Aminonitrile which has a dinitrile weight content of 0.0050% can be obtained by distillation, but this low content is obtained at the cost of the quantity of aminonitrile that is available, because intermediate distillation fractions must be separated, which can be recycled into a new hemihydrogenation operation. It is thus generally preferred to use in the cyclizing hydrolysis stage an aminonitrile containing from 0.005% to 5% by weight of dinitrile.

It is generally difficult, using distillation, to have in the aminonitrile an overall content of the other by-products which is lower than 0.2% although this value does not constitute a critical lower limit in the case of the process of the invention.

An aminonitrile containing from 0.2% to 5% by weight of by-products containing an imine or amine functional group is generally introduced into the cyclizing hydrolysis stage.

The diamine corresponding to the dinitrile used does not interfere in the cyclizing hydrolysis stage. In the present text it is not considered as a by-product containing an amine functional group, referred to above.

The aliphatic dinitriles which may be used in the first stage of the process of the invention are more particularly the dinitriles of general formula (I):

$$NC-R-CN \qquad (I)$$

in which R denotes a linear or branched alkylene or alkenylene group containing from 1 to 12 carbon atoms.

Dinitriles of formula (I) in which R denotes a linear or branched alkylene radical containing from 1 to 6 carbon atoms are preferably used.

By way of examples of such dinitriles there may be mentioned especially adiponitrile, methylglutaronitrile, ethylsuccinonitrile, malononitrile, succinonitrile and glutaronitrile and their mixtures, especially the mixtures of adiponitrile and/or of methylglutaronitrile and/or of ethylsuccinonitrile which are liable to originate from the same process for the synthesis of adiponitrile.

In practice the case where $R=(CH_2)_4$ will be the most frequent because this corresponds to the use of adiponitrile (ADN) in the present process.

The hemihydrogenation of the dinitrile to corresponding aminonitrile, with the aid of hydrogen, is generally performed in the presence of a catalyst based on Raney nickel, Raney cobalt, Raney nickel or on Raney nickel or Raney cobalt containing a dopant element chosen from the elements of groups IVb, VIb, VIIb and VIII of the Periodic Classification of the elements as published in the Handbook of Chemistry and Physics, 51st Edition (1970–1971) and from a strong mineral base derived from an alkali or alkaline-earth metal.

The initial hydrogenation mixture contains at least one solvent capable of at least partially solubilizing the dinitrile, because the hydrogenation is carried out better when the said dinitrile is dissolved. This solvent medium may consist of water in a proportion of at least 0.5% by weight relative to the totality of the liquid compounds of the reaction mixture.

As a complement or replacement for water the reaction mixture may contain at least one other solvent such as an alcohol and/or an amide and/or an amine and/or ammonia. Alcohols which are more particularly suited are alkanols like methanol, ethanol, 1-propanol, 2-propanol and 1-butanol, diols like ethylene glycol and propylene glycol, polyols or the mixtures of the said alcohols. In the case where the solvent is an amide it is possible to use, in particular, dimethylformamide and dimethylacetamide. Among the amines which may be employed as solvent, it is possible to use, for example, the diamine or the aminonitrile corresponding to the dinitrile which is hydrogenated.

When it is employed with water, the solvent represents, by weight, from two to four times the weight of the water.

According to a preferred alternative form of the stage of hemihydrogenation of the dinitrile, the initial reaction mixture includes the diamine and/or the aminonitriles that are liable to be formed from the dinitrile to be hydrogenated and unconverted dinitrile, in a proportion of 80% to 99.5% in the case of these three compounds combined.

The degree of conversion of the dinitrile is preferably at least 70%.

The strong inorganic base generally consists of alkali metal or alkaline-earth metal hydroxides, carbonates and alkanolates. It is preferably chosen from alkali metal hydroxides, carbonates and alkanolates. As a matter of priority, the strong inorganic base used is chosen from the following compounds: LiOH, NaOH, KOH, RbOH, CsOH and their mixtures.

In practice NaOH and KOH are used in most cases, for a good performance-price compromise, although RbOH and CsOH can give very good results.

The reaction mixture has a composition that varies depending on the type of embodiment of the process.

In fact, if the process is used noncontinuously, as is the case in laboratory implementations or intermittent small-scale manufacturing operations, the initial reaction mixture will gradually become richer in aminonitrile and, in a smaller proportion, in diamine, whereas the dinitrile concentration may either decrease if all or most of the said dinitrile is charged as soon as the hemihydrogenation begins, or may remain relatively constant if the dinitrile is introduced gradually during the reaction.

On the other hand, if the process is conducted continuously, the composition of the reaction mixture leaving the reactor reaches values that are determined by the selectivities of the reaction.

The water is usually present in a quantity smaller than or equal to 20%. The water content of the reaction mixture is preferably between 2% and 15% by weight relative to the combined liquid constituents of the said mixture.

In continuous operation of the process of the invention the average composition will be determined by the ratio of the respective selectivities for aminonitrile and diamine and by the rate of introduction of the dinitrile.

The quantity of strong inorganic base is advantageously higher than or equal to 0.1 mol/kg of catalyst. It is preferably between 0.1 mol and 3 mol per kg of catalyst and still more preferably between 0.3 and 2 mol/kg of catalyst.

The catalyst employed in the process may be a Raney nickel, a Raney cobalt, a Raney nickel or a Raney cobalt comprising, besides the nickel or the cobalt and the residual quantities of the metal removed from the original alloy during the preparation of the catalyst, that is to say generally aluminium, one or several other elements, often called dopants, such as, for example, chromium, titanium, molybdenum, tungsten, iron and zinc. Chromium and/or iron and/or titanium are considered to be the most advantageous ones of these dopant elements. These dopants usually represent from 0% to 15% and preferably from 0% to 10% by weight per weight of nickel.

The quantity of catalyst used may vary very widely as a function especially of the method of operation which is adopted or of the reaction conditions which are chosen. Thus, if the dinitrile is introduced gradually into the reaction mixture the weight ratio catalyst/dinitrile to be hydrogenated will be much higher than if all the dinitrile is introduced as soon as the reaction begins. To give an indication, from 0.5% to 50% by weight of catalyst may be employed relative to the total weight of the reaction mixture, and in most cases from 1% to 35%.

In the case of a given catalyst and with a given degree of conversion of the dinitrile, the aminonitrile yield passes through a maximum which is determined by the base/Ni or base/Co ratio.

The aminonitrile yield optimum, at constant degree of conversion of the dinitrile, depends on the nature and the content of the dopant, on the quantity of water in the reaction mixture and on the temperature.

The hemihydrogenation stage of the process of the invention is generally performed at a reaction temperature which is lower than or equal to 150° C., preferably lower than or equal to 120° C. and, still more preferably, lower than or equal to 100° C.

In concrete terms, this temperature is between the ambient temperature (approximately 20° C.) and 100° C. It is possible to operate at a temperature lower than 20° C. without any technical problem, but this offers no advantage because of a lower output efficiency of the reaction.

Before, simultaneously with or after the heating, the reaction vessel is brought to the appropriate hydrogen pressure, that is to say, in practice, of between 1 bar (0.10 MPa) and 100 bar (10 MPa) and preferably between 5 bar (0.5 MPa) and 50 bar (5 MPa).

The reaction period can vary as a function of the reaction conditions and of the catalyst.

In noncontinuous operation it may vary from a few minutes to several hours.

In continuous operation, which constitutes the preferable industrial method for the process according to the invention, the duration is obviously not a parameter than can be set.

Before subjecting the aminonitrile obtained in the hemihydrogenation stage to the cyclizing hydrolysis stage in order to form the lactam, it is necessary to remove most of the water and/or of the solvent which may be present, of the dinitrile which has not reacted, of the diamine which is also formed and of the reaction by-products such as the compounds of imine or amine type.

This purification may be conveniently carried out by a conventional distillation operation, preferably conducted at a pressure which is lower than atmospheric pressure. The water and/or the solvent distil first of all, followed by the diamine formed, for example hexamethylenediamine. The aminonitrile comes next, for example 6-aminocapronitrile (ACN), while the unreacted dinitrile may or may not be also separated by distillation.

For its use in the cyclizing hydrolysis reaction the aminonitrile obtained by this distillation may contain, as has already been stated above, up to 10% by weight and preferably up to 5%, of dinitrile and up to 10% by weight and preferably up to 5%, of other by-products which are formed during the hydrogenation of the dinitrile.

When the dinitrile is adiponitrile, these by-products may be especially hexamethyleneimine (HMI), aminomethylcyclopentylamine (AMCPA), azacycloheptene (AZCHe), 1-imino-2-cyanocyclopentane (ICCP), diaminocyclohexane (DCH), bis(hexamethylenetriamine) (BHT), the product of condensation of azacycloheptene with 6-aminocapronitrile (6-(6'-aminohexamethylene-imino)hexanenitrile) or, when the hemihydrogenation is conducted in an alcohol, various compounds from reaction of this alcohol with reaction intermediates.

The stage of cyclizing hydrolysis of the purified aminonitrile, for the purpose of preparing the corresponding lactam, consists of a vapour phase reaction of the said aliphatic aminonitrile of general formula (II):

$$M\!\!=\!\!C\!\!-\!\!R\!\!-\!\!CH_2\!\!-\!\!NH_2 \qquad (II)$$

in which R denotes a linear or branched alkylene or alkenylene radical containing from 1 to 12 carbon atoms, with water, preferably in the presence of a solid catalyst.

In the formula (II) of the aminonitrile R preferably denotes a linear or branched alkylene radical containing from 1 to 6 carbon atoms.

The solid catalyst may be of very varied nature. A molecular sieve (crystalline compound with a microporosity of approximately 3 to 10 angstroms), a nonzeolite molecular sieve, a metal phosphate or an acidic or amphoteric bulk oxide may be employed.

The molecular sieves are silicalites and acidic zeolites.

A zeolite is intended to mean a crystalline tectosilicate of natural or synthetic origin in which the crystals result from the three-dimensional assembly of tetrahedral $SiO_4$ and $TO_4$ units, T denoting a trivalent element such as aluminium, gallium, boron and iron, preferably aluminium. Zeolites of aluminosilicate type are the most common ones.

Within the crystal lattice the zeolites exhibit a system of cavities connected to one another by channels of a well-defined diameter, which are called pores.

Zeolites may exhibit a one-dimensional, two-dimensional or three-dimensional lattice.

Among the zeolites it is possible to employ natural zeolites like, for example, offretite, clinoptilotite, erionite, chabazite and philipsite.

Synthetic zeolites are also quite suitable.

As examples of synthetic zeolites with a one-dimensional lattice there may be mentioned, among others, zeolite ZSM-4, zeolite L, zeolite ZSM-12, zeolite ZSM-22, zeolite ZSM-23 and zeolite ZSM-48.

By way of examples of zeolites with a two-dimensional lattice which are employed preferentially there may be mentioned beta zeolite, mordenite and ferrierite.

Insofar as the zeolites with a three-dimensional lattice are concerned, there may be mentioned more particularly zeolite Y, zeolite X, zeolite ZSM-5, zeolite ZSM-11 and offretire.

Use is made preferably of synthetic zeolites and more particularly of those which are in the following forms:

mazzite of Si/Al molar ratio of 3.4 zeolite L of Si/Al molar ratio of 1.5 to 3.5 mordenite of Si/Al molar ratio of 5 to 15 ferrierite of Si/Al molar ratio of 3 to 10 offretire of Si/Al molar ratio of 4 to 8.5 beta zeolites of Si/Al molar ratio of 15 to 25 zeolites Y, in particular the zeolites obtained after dealumination treatment (for example hydrotreatment, washing with the aid of hydrochloric acid or treatment with $SiCl_4$), more particularly zeolites US-Y of Si/Al molar ratio higher than 3, preferably between 6 and 60 zeolite X of faujasite type of Si/Al molar ratio from 0.7 to 1.5 zeolites ZSM-5 or aluminium silicalite of Si/Al molar ratio of 10 to 2000 zeolite ZSM-11 of molar ratio of 5 to 30.

The zeolites used in the present process are known products described in the literature [cf. Atlas of zeolites structure types by W. M. Meier and D. H. Olson, published by the Structure Commission of the International Zeolite Association (1978)].

Zeolites which are available in the trade may be used or they may be synthesized according to the processes described in the literature.

Preference may be made to the abovementioned Atlas and more particularly, for the preparation:

of zeolite L to the publication by R. M. Barrer et al., Z. Kristallogr. 128, pp 352 et seq. (1969)

of zeolite ZSM-12, to U.S. Pat. No. 3,832,449 and to the paper by Lapierre et al., Zeolites 5, pp 346 et seq. (1985)

of zeolite ZSM-22, to the publication by G. T. Kokotailo et al., Zeolites 5, pp 349 et seq. (1985)

of zeolite ZSM-23, to U.S. Pat. No. 4,076,842 and to the paper by A. C. Rohrman et al., Zeolites 5, pp 352 et seq. (1985)

of zeolite ZSM-48, to the work by J. L. Schlenker et al., Zeolites 5, pp 355 et seq. (1985)

of beta zeolite, to U.S. Pat. No. 3,308,069 and to the paper by P. Caullet et al., Zeolites 12, pp 240 et seq. (1992)

of mordenite, to the work by Itabashi et al., Zeolites 6, pp 30 et seq. (1986)

of zeolites X and Y, to Patents U.S. Pat. No. 4,076,842 and U.S. Pat. No. 3,130,007 respectively of zeolite ZSM-5, to U.S. Pat. No. 3,702,886 and to the paper by V. P. Shiralkar et al., Zeolites 9, pp 363 et seq. (1989)

of zeolite ZSM-11, to the work by I. D. Harrison et al., Zeolites 7, pp 21 et seq. (1987).

The zeolites may be employed in various forms: powder, shaped products such as granules (for example cylinders or beads), tablets or monoliths (honeycomb-shaped blocks), which are obtained by extrusion, moulding, pressing or any other known process type. In practice, on industrial scale, it is the forms of granules, of beads or of monoliths which offer most advantages both from the viewpoint of effectiveness and from the viewpoint of convenience in use.

The invention does not rule out the presence of binders employed during the forming of the zeolite, for example aluminas or clays.

Whatever the zeolite chosen, a treatment which makes it acidic is carried out if necessary. Conventional treatments are relied on for this purpose.

Thus, the alkaline cations can be exchanged by subjecting the zeolite to a treatment carried out with aqueous ammonia, thus resulting in an exchange of alkali metal cation with an ammonium ion, and then to calcining the exchanged zeolite in order to decompose the ammonium cation thermally and to replace it with an $H^+$ ion.

The quantity of aqueous ammonia to be used is at least equal to the quantity necessary for exchanging all the alkali metal cations with ammonium ions. At least from $10^{-5}$ to $5 \times 10^{-3}$ moles of aqueous ammonia are therefore used per gram of zeolite.

Among the silicalites use is made more particularly of the silicalite of type 1, of structure which is similar to ZSM-5, silicalite of type 2, of structure which is similar to ZSM-11, and beta silicalite.

The term "nonzeolitic molecular sieve" or NZMS includes, in the present text, the SAPO molecular sieves described in U.S. Pat. No. 4,440,871, the ELAPSO molecular sieves described in Patent EP-A-0 159 624 and some crystalline aluminophosphates and metalloaluminophosphates (MeAPO), ferroaluminophosphates (FeAPO) and titanoaluminophosphates (TAPO) described in patents which are indicated below. The crystalline aluminophosphates are described in U.S. Pat. No. 4,310,440; the crystalline metalloaluminophosphates MeAPO, Me denoting at least one metal chosen from Mg, Mn, Co and Zn, are described in U.S. Pat. No. 4,567,029; the crystalline ferroaluminophosphates FeAPO are described in U.S. Pat. No. 4,554,143; the titanoaluminophosphates TAPO are described in U.S. Pat. No. 4,500,651, and other nonzeolitic molecular sieves ELAPO are described in Patents EP-A-0 158 976 and EP-A-0 158 349.

The metal phosphate may be more precisely a metal phosphate of general formula (III):

$$MH_h(PO_4)_n \cdot (Imp)_p \qquad \text{(III)}$$

in which:

M denotes a divalent, trivalent, tetravalent or pentavalent element chosen from groups 2a, 3b, 4b, 5b, 6b, 7b, 8, 2b, 3a, 4a and 5a of the Periodic Classification of the elements or a mixture of several of these elements or M=O when M denotes certain pentavalent elements, Imp denotes a basic impregnating compound consisting of an alkali metal or alkaline-earth metal, or of mixtures of several of these metals, used in combination with a counteranion to ensure electrical neutrality, n denotes 1, 2 or 3, h denotes 0, 1 or 2, p denotes a number between 0 and ⅓ and corresponds to a molar ratio of the impregnating compound Imp to the impregnated $MH_h(PO_4)_n$.

Among the aminonitriles of formula (II) the most important ones are those which produce the lactams used as raw material for the preparation of polyamides 4, 5, 6 and 10, that is to say those in whose formula the symbol R denotes a linear alkylene radical containing 2, 3, 4 or 8 carbon atoms. The preferred compound of formula (II) is 6-aminocapronitrile (or epsilon-capronitrile), which produces caprolactam, the polymerization of which yields polyamide 6.

Among the metals of groups 2a, 3b, 4b, 5b, 6b, 7b, 8, 2b, 3a, 4a and 5a of the Periodic Classification of the elements it is possible to mention especially beryllium, magnesium, calcium, strontium, barium, aluminium, boron, gallium, indium, yttrium, lanthanides such as lanthanum, cerium, praseodymium, neodymium, samarium, europium, gadolinium, terbium, dysprosium, holmium, erbium, thulium, ytterbium and lutetium, zirconium, titanium, vanadium, niobium, iron, germanium, tin and bismuth.

Among the lanthanide phosphates it is possible to discern a first class which contains the orthophosphates of light rare earths, also called ceric rare earths, including lanthanum, cerium, praseodymium, neodymium, samarium and europium. These orthophosphates are dimorphic. They have a hexagonal structure and change towards a monoclinic structure when heated to a temperature of 600° to 800° C.

A second class of lanthanide phosphates contains gadolinium, terbium and dysprosium orthophosphates. These orthophosphates have the same structure as the orthophosphates of ceric rare earths but in addition have a third crystalline phase of tetragonal structure at high temperature (towards 1700° C.).

A third class of lanthanide phosphates contains the orthophosphates of heavy rare earths, also called yttric rare earths, including yttrium, holmium, erbium, thulium, ytterbium and lutetium. These compounds crystallize only in the tetragonal form.

Among the abovementioned various classes of rare earth orthophosphates use is made preferably of ceric rare earth orthophosphates.

It is possible to use metal phosphates of formula (II) which are mixtures of phosphates of several of the metals indicated above or mixed phosphates of several of the metals indicated above or alternatively mixed phosphates containing one or more of the metals indicated above and one or more other metals such as alkali or alkaline-earth metals.

The counteranions forming part of the formula of the impregnating compound Imp are basic. Hydroxide, phosphate, hydrogenphosphate, dihydrogenphosphate, chloride, fluoride, nitrate, benzoate and oxalate ions may be used in particular, no limitation being implied by these mentions.

The molar ratio p is preferably between 0.02 and 0.2.

If reference is made to the general techniques for the preparation of phosphates (as described especially in P.

Pascal "Nouveau traité de chimie minérale" [New treatise on inorganic chemistry] volume X (3.956), pages 821–823 and in "Gmelins Handbuch der anorganischen Chemie" [Gmelins Handbook of inorganic chemistry] (8th edition) volume 16 (C), pages 202–206 (1965), two main routes of access to phosphates can be discerned. On the one hand, the precipitation of a soluble salt of the metal (chloride, nitrate) with ammonium hydrogenphosphate or phosphoric acid. On the other hand, dissolving the oxide or carbonate of the metal (which are insoluble) with phosphoric acid, generally with heating, followed by reprecipitation.

The precipitated phosphates obtained according to one of the indicated routes may be dried, treated with an organic base (such as aqueous ammonia) or inorganic base (such as an alkali metal hydroxide) and subjected to a calcination, it being possible for these three operations to be carried out in the order shown or in a different order.

The metal phosphates of formula (III) in the case of which the symbol p is greater than 0 can be prepared by impregnation of the compound $MH_h(PO_4)_n$, prepared according to one of the techniques described above, with a solution or suspension of Imp in a volatile solvent such as, preferably, water.

The results are proportionately better the more soluble Imp is and the more freshly manufactured is the compound $MH_h(PO_4)_n$.

Thus, an advantageous process for the preparation of the phosphates of formula (II) consists:

a) in carrying out the synthesis of the compound $MN_h(PO_4)_n$; then, preferably without isolating $MH_h(PO_4)_n$ from the reaction mixture;

b) in introducing the impregnating compound Imp into the reaction mixture;

c) in separating any residual liquid from the reaction solid;

d) in drying and, optionally, calcining.

The performance of the catalyst of formula (III) and especially its resistance to deactivation can be improved still further by a calcination. The calcination temperature will be advantageously between 300° C. and 1000° C. and preferably between 400° C. and 900° C. The calcination period may vary within wide limits. To give an idea, it is generally between 1 hour and 24 hours.

Among the catalysts of formula (III) which are preferred in the process of the invention it is possible to mention more particularly lanthanum phosphate, calcined lanthanum phosphate, lanthanum phosphate used in combination with a caesium, rubidium or potassium derivative, calcined cerium phosphate, cerium phosphate used in combination with a caesium, rubidium or potassium compound, samarium phosphate used in combination with a caesium, rubidium or potassium compound, aluminium phosphate, aluminium phosphate, aluminium phosphate used in combination with a caesium, rubidium or potassium compound, calcined niobium phosphate, niobium phosphate used in combination with a caesium, rubidium or potassium compound, calcined zirconium hydrogenphosphate and zirconium hydrogenphosphate used in combination with a caesium, rubidium or potassium compound.

The acidic bulk oxides which can be used as solid catalysts in the cyclizing hydrolysis stage are especially metal oxides, mixtures of metal oxides or metal oxides modified to make them acidic, especially by the action of a dihalide, an ammonium halide or an acid like sulphuric acid or hydrogenhalide acids. The halogen which may thus be introduced to acidify the bulk oxide is preferably chlorine or fluorine.

The amphoteric bulk oxides are the oxides of amphoteric nature or those made amphoteric by their method of preparation or by a subsequent treatment.

By way of nonlimiting examples of acid or amphoteric bulk oxides there may be mentioned the mixtures $SiO_2/Al_2O_3$, $SiO_2/Ga_2O_3$, $SiO_2/Fe_2O_3$ and $SiO_2/B_2O_3$, halogenated aluminas such as especially chlorinated aluminas and fluorinated aluminas, sulphated zirconia, niobium oxide, tungsten oxide, thoria, zirconia, titanium dioxide, ceria, silicas and aluminas.

Among these bulk oxides, the aluminas which may be employed as solid catalysts in the cyclizing hydrolysis stage are of very varied structure. However, it is preferable to choose, among the various aluminas which are active in this reaction, those which are deactivated least. This is why the choice preferably falls on aluminas which have a specific surface measured by the BET method which is higher than or equal to 5 m²/g and still more preferably higher than or equal to 10 m²/g.

The alumina used in the process of the invention preferably has a specific surface equal to or lower than 500 m²/g.

The aluminas which may be employed in the present process are first of all the aluminas which have a specific surface higher than or equal to 10 m²/g and lower than or equal to 280 m²/g as well as a volume of the pores of diameter greater than 500 angstroms which is higher than or equal to 10 ml/100 g.

The BET specific surface is the specific surface determined by nitrogen adsorption in accordance with ASTM standard D 3663-78 established on the basis of the Brunauer-Emmett-Teller method described in the periodical "Journal of the American Chemical Society", 60, 309 (1938).

The volume of the pores of diameter greater than 500 Å represents the cumulative volume created by all the pores of size greater than a diameter of 500 Å. This volume is measured by the mercury penetration technique, in which Kelvin's law is applied.

The aluminas of this first class preferably have a volume of the pores of diameter greater than 500 Å higher than or equal to 20 ml/100 g and still more preferably higher than or equal to 30 ml/100 g.

The aluminas of this first class also preferably have a specific surface higher than or equal to 50 m²/g.

The aluminas which can be employed in the present process are also the aluminas which have a specific surface higher than or equal to 50 m²/g and lower than or equal to 280 m²/g and a volume of pores of diameter greater than 70 angstroms which is higher than or equal to 30 ml/100 g.

The aluminas of this second class preferably have a volume of pores of diameter greater than 70 Å higher than or equal to 45 ml/100 g.

The aluminas of this second class also preferably have a specific surface higher than or equal to 80 m²/g.

The aluminas which can be employed in the present process are also the aluminas which have a specific surface higher than or equal to 280 m²/g as well as a total pore volume higher than or equal to 15 ml/100 g.

The aluminas of this third class preferably have a total pore volume higher than or equal to 22 ml/100 g and still more preferably higher than or equal to 30 ml/100 g.

The aluminas are also characterized by their acidity.

This acidity can be measured by the test for isomerization of 1-butene to 2-butene.

This test is based on the reaction of isomerization of 1-butene to a mixture of cis-2-butene and trans-2-butene at a temperature T (T=400° C. in the present case).

The isomerization reaction is a thermodynamic equilibrium. Two constants can be defined:

the theoretical equilibrium constant Kth(T) determined by the calculation:

$$Kth(T) = \frac{[cis-2-butene]eq + [trans-2-butene]eq}{[1-butene]eq + [cis-2-butene]eq + [trans-2-butene]eq}$$

where [butene]eq denotes the concentration of each of the isomers in equilibrium at the temperature T;

the actual equilibrium constant K(T) determined by the result of the measurements:

$$K(T) = \frac{[cis-2-butene] + [trans-2-butene]}{[1-butene] + [cis-2-butene] + [trans-2-butene]}$$

where [butene] denotes the concentration of each of the isomers leaving the reactor at the temperature T.

The isomerizing power A of the aluminas is defined by the activity in relation to the equilibrium:

$$A(T) = \frac{K(T)}{Kth(T)} \times 100$$

In practice the test is carried out in a vapour phase reactor operating in a pulse mode, into which are introduced 500 mg of ground alumina (particles of between 400 and 500 μm). The alumina is conditioned for 2 hours at 250° C. under a stream of helium with a flow rate of 2.5 liters/hour. The alumina is then heated to a temperature of 400° C. and 1 milliliter of 1-butene is injected upstream of it into the helium flow. Analysis of the exit gases is carried out by gas phase chromatography and enables the quantities of 1-butene and of cis and trans 2-butene which are recovered to be measured.

This isomerizing power A is corrected for the isomerizing power obtained in the same conditions with the empty reactor. The corrected isomerizing power $A_c$ represents the acidity of the said aluminas.

When the alkali metal or alkaline-earth metal content present in the alumina is lower than 60 mmol per 100 g of alumina, the higher the value of $A_c$, the more acidic is the alumina.

Aluminas are generally obtained by dehydration of gibbsite, bayerite, nordstrandite or of their various mixtures. Reference may be made, for example, to the Kirk-Othmer encyclopedia, volume 2, pages 291–297.

The aluminas used in the present process can be prepared by bringing a hydrated alumina, in finely divided form, into contact with a stream of hot gas at a temperature of between 400° C. and 1000° C., and then maintaining the contact between the hydrate and the gases for a period ranging from a fraction of a second to 10 seconds and, finally, separation of the partially dehydrated alumina and of the hot gases. Reference may be made in particular to the process described in U.S. Pat. No. 2,915,365.

It is also possible to undertake the autoclaving of agglomerates of the aluminas obtained above, in aqueous medium, optionally in the presence of acid, at a temperature higher than 100° C. and preferably between 150° C. and 250° C., for a period preferably of between 1 and 20 hours, and then their drying and their calcination.

The calcination temperature is adjusted so that specific surfaces and pore volumes which are within the value regions indicated above are obtained.

Because of their main processes of manufacture, the aluminas used in the present process contain, in most cases, sodium, the content of which is usually expressed as weight of Na$_2$O relative to the weight of the alumina.

The catalyst may be used in various forms, such as powder, beads, crushed material, extrudates or tablets, it being possible for the forming to be optionally carried out with the aid of a binder.

It may be, first of all, alumina beads originating from oil-drop forming (or coagulation in drops). Beads of this type can, for example, be prepared by a process according to the teaching of Patents EP-A-0 015 801 or EP-A-0 097 539. The control of the porosity may be carried out, in particular, according to the process described in Patent EP-A-0 097 539, by drop coagulation of an aqueous suspension or dispersion of alumina or of a solution of a basic aluminium salt which is in the form of an emulsion consisting of an organic phase, an aqueous phase and a surface agent or an emulsifier. The said organic phase may, in particular, be a hydrocarbon.

It may also be crushed alumina material. This crushed material may originate from the crushing of any type of alumina-based material such as, for example, beads obtained by any type of process (oil-drop, pelletizer or rotary drum) or of extrudates. The control of the porosity of this crushed material is carried out by the choice of the alumina-based material which is crushed in order to obtain it.

It may also be alumina extrudates. These can be obtained by blending followed by the extrusion of an alumina-based material, it being possible for the said material to originate from the fast dehydration of hydrargillite or the precipitation of an alumina gel. The control of the porosity of these extrudates may be carried out through the choice of the alumina used and through the conditions of preparation of this alumina or through the conditions of blending of this alumina before extrusion. The alumina may thus be mixed during the blending with pore-formers. By way of example, the extrudates may be prepared by the process described in U.S. Pat. No. 3,856,708.

In some cases it may be advantageous for at least a proportion of the free volume of the reactor to be occupied by an inert solid such as, for example, quartz, in order to promote the vaporization and the dispersion of the reactants.

As in the case of the aluminas, the solid catalyst of the cyclizing hydrolysis stage is generally used in the form of powder, of tablets, of crushed material, of beads or of extrudates, it being possible for the said forming to be optionally carried out with the aid of a binder. In some cases it may be advantageous for at least a proportion of the free volume of the reactor to be occupied by an inert solid such as, for example, quartz, in order to promote the vaporization and the dispersion of the reactants.

The cyclizing hydrolysis reaction requires water to be present. The molar ratio of the water to the aminonitrile introduced is usually between 0.5 and 50 and preferably between 1 and 20. The upper value of this ratio is not critical for the invention but higher ratios are hardly of interest because of economic questions.

The aminonitrile and the water may be introduced in the form of their mixtures in the vapour state or may be introduced separately into the reactor. It is possible to carry out a prevaporization of the reactants which subsequently move into a mixing chamber.

Any inert gas, such as nitrogen, helium or argon, may be employed as carrier without disadvantage.

The temperature at which the cyclizing hydrolysis stage is carried out must be sufficient to ensure that the reactants are in the vapour state. It generally lies between 200° C. and 450° C. and preferably between 250° C. and 400° C.

The period of contact between the aminonitrile and the catalyst is not critical. It can vary, in particular, according to the apparatus employed. This contact time is preferably between 0.5 and 200 seconds and still more preferably between 1 and 100 seconds.

Pressure is not a critical parameter in this stage of the process. It is thus possible to operate at pressures of $10^{-3}$ bar to 200 bar. The process will be preferably carried out at a pressure of 0.1 to 20 bar.

It is not ruled out to employ a solvent which is inert in the reaction conditions, such as for example an alkane, a cycloalkane, an aromatic hydrocarbon or one of these above hydrocarbons, halogenated, and thus to have a liquid phase in the reaction stream.

The lactam obtained by the process according to the invention may be purified, generally by distillation, before being polymerized. This purification is much easier at the lactam stage than at the aminonitrile stage. It is found, furthermore, that the by-products present in the aminonitrile introduced into the cyclizing hydrolysis stage are, to a large degree, decomposed during this stage and are then easily removed.

The distillation of the lactam may be carried out in particular in the presence of a strong base such as an alkali metal hydroxide, the presence of this base making it easier to separate the lactam from the by-products and from the aminonitrile which may not have been converted. Sodium hydroxide or potassium hydroxide is particularly suitable.

The examples which follow illustrate the invention.

EXAMPLE 1

The following are charged into a 3.6–1 stainless steel reactor fitted with stirring of Rushtone Cavitator type, means for introducing the reactants and hydrogen and a temperature control system:

adiponitrile 1710 g hexamethylenediamine 574.4 g water 253 g

KOH 0.63 g

Raney Ni (containing 1.7% of Cr) 30.3 g of Ni

In this example there is 0.4 mol KOH/kg Ni.

The reaction mixture is heated to 50° C. after the reactor has been purged with nitrogen and then with hydrogen; the pressure is then controlled at 2 MPa at this temperature by continuous addition of hydrogen. The progress of the reaction is followed using hydrogen consumption. When 2.2 equivalents of hydrogen, relative to the adiponitrile charged, have been consumed, the reaction is stopped by stopping the stirring and cooling the reaction mixture. The remaining adiponitrile (ADN) and the 6-aminocapronitrile (ACN) formed are determined by vapour phase chromatography and the degree of conversion (DC) of the ADN and the yield of ACN, in relation to the ADN converted (CY) are calculated.

The following results are obtained:

reaction period: 118 min

DC of ADN: 81%

CY of ACN: 60.3%

This operation is repeated 7 times and all the reaction masses, after separation of the catalyst by filtration, are combined to be distilled. Aminocapronitrile is distilled at 120° C. at 2660 Pa, with the aid of a column 70 mm in diameter, with stainless steel packing, which has an efficiency, corresponding to 30 theoretical plates.

The aminonitrile thus obtained contains:

less than 0.01% by weight of adiponitrile 0.1% by weight of hexamethylenediamine 98.4% by weight of 6-aminocapronitrile 1.5% by weight of various amines and imines, the main one of which is 6-(6'-aminohexamethyleneimino) hexanenitrile.

The stage of cyclizing hydrolysis of the 6-aminocapronitrile (ACN) thus prepared is carried out in a 20-ml cylindrical reactor made of Pyrex glass, arranged vertically and fitted with means for heating, openings for the entry and exit of the gas flows and an injection system for the reactants.

Into this reactor are charged in succession 10 ml of quartz, 1 ml of alumina in the form of powder of particle size of 400–500 micrometers and, again, 10 ml of quartz.

Thus charged, the reactor is heated to 400° C. under a stream of air (with a flow rate of 1.5 liters/hour) for 2 hours. The reactor is then cooled to 320° C. (chosen reaction temperature) and placed under a stream of nitrogen (flow rate of 17.6 ml/min).

A mixture of ACN and water (50/50 weight ratio, that is a water/ACN molar ratio of 6.2) is then injected with the aid of a pump. The injection rate of the mixture is 1.14 g/h.

At the reactor exit the vapour is condensed in a glass trap at ambient temperature.

The final reaction mixture is determined by gas phase chromatography.

The degree of conversion (DC) of aminocapronitrile and the yield (CY) of caprolactam (CPL) in relation to the aminocapronitrile converted are determined.

The complete disappearance of the amine and imine by-products present in the aminocapronitrile used is ascertained by various analytical techniques (gas phase chromatography coupled with mass spectrometry and nuclear magnetic resonance in particular).

The following stable performance is obtained in the case of a reaction period of 50 hours:

DC of ACN: $\geq 99\%$

CY of CPL: $\geq 98\%$

EXAMPLE 2

The following charges are introduced into a metal reactor fitted with a cavitator-type stirring system, means for introducing reactants and hydrogen and various control systems:

adiponitrile 2856 kg hexamethylenediamine 1151 kg water 588 kg

KOH 0.83 kg

Raney Ni (containing 1.7% of Cr) 37 kg

In this example there is 0.4 mol KOH/kg Ni.

The operation is carried out in the conditions described in the case of Example 1.

The following results are obtained:

reaction period: 3 h 30 min

DC of ADN: 86%

CY of ACN: 64%

After separation of the catalyst by filtration approximately 6 kg of reaction mixture are distilled at 120° C. at 2660 Pa with the aid of a column mm in diameter, with stainless steel packing, which has an efficiency corresponding to 11 theoretical plates.

For the second part of the process a fraction from the preceding distillation is employed, which contains:

0.02% by weight of adiponitrile 0.36% by weight of hexamethylenediamine 97.1% by weight of 6-aminocapronitrile 2.5% by weight of various amines and imines, the main one of which is 6-(6'-aminohexamethyleneimino) hexanenitrile.

In order to demonstrate better that the process of the invention makes it possible to use in the cyclizing hydrolysis stage a 6-aminocapronitrile which is not highly purified, various additional impurities were added to this fraction of distilled aminocapronitrile (ACN). An ACN containing the following is thus obtained:

1% by weight of adiponitrile

1% by weight of hexamethylenediamine 2.5% by weight of various amines and imines the main one of which is 6-(6'-aminohexamethyleneimino) hexanenitrile 1% by weight of 1-imino-2-cyanacyclopentane 1% by weight of hexamethyleneimine (HMI)

1% by weight of bis(hexamethylenetriamine) (BHT)

92.5% by weight of 6-aminocapronitrile.

The stage of cyclizing hydrolysis of the ACN thus prepared is carried out in a 20-ml cylindrical reactor made of Pyrex glass, arranged vertically and fitted with means for heating, openings for the entry and exit of the gas flows and a system for injecting reactants.

Into this reactor are charged in succession 3 ml of quartz, 2 ml (0.87 g) of alumina (of BET specific surface of 130 $m^2/g$) in the form of powder of particle size of 300–600 micrometers and, again, 5 ml of quartz.

Thus charged, the reactor is heated to 400° C. under a stream of air (with a flow rate of 1.5 liters/hour) for 2 hours. The reactor is then cooled to 320° C. (chosen reaction temperature) and placed under a stream of nitrogen (flow rate of 88 ml/min).

A mixture of ACN and water (water/ACN molar ratio of 1.1) is then injected with the aid of a pump. The rate of injection of the mixture is 11 g/h.

At the reactor exit the vapour is condensed in a glass trap at ambient temperature.

The final reaction mixture is determined by gas phase chromatography.

The degree of conversion (DC) of aminocapronitrile and the yield (CY) of caprolactam (CPL) in relation to the aminocapronitrile converted are determined.

The complete disappearance of the amine and imine by-products present in the aminocapronitrile used is ascertained by various techniques of analysis (gas phase chromatography coupled with mass spectrometry and nuclear magnetic resonance in particular).

The following stable performance is obtained in the case of a reaction period of 7 hours:

DC of ACN: 63%

CY of CPL: 100%

I claim:

1. A process for the preparation of a lactam comprising:
   hemihydrogenating an aliphatic dinitrile to form an aminonitrile in the presence of a catalyst;
   distilling the aminonitrile so that the dinitrile content is less than or equal to 10% by weight and the content of by-products containing an amine or imine functional group is less than or equal to 10% by weight; and
   hydrolyzing the distilled aminonitrile with water in the vapor phase in the presence or the absence of a catalyst to form said lactam.

2. The process according to claim 1, wherein the aliphatic dinitrile corresponds to formula (I):

$$NC-R-CN \quad (I)$$

in which R denotes a linear or branched alkylene or alkylene group containing from 1 to 12 carbon atoms.

3. The process according to claim 2, wherein the linear or branched alkylene or alkylene group contains from 1 to 6 carbon atoms.

4. The process according to claim 1, wherein the hemihydrogenating catalyst is a Raney nickel catalyst, Raney cobalt catalyst, or a Raney cobalt catalyst containing a dopant, wherein said dopant is an element of group IVb, group VIb, group VIIb or group VIII of the Periodic Classification of elements, or a strong inorganic base derived from an alkali metal or an alkaline earth metal.

5. The process according to claim 4, wherein the strong organic base is an alkali metal or alkaline earth metal hydroxide, carbonate or alkanolate.

6. The process according to claim 5, wherein the strong base is an alkali metal hydroxide, carbonate or alkanolate.

7. The process according to claim 4, wherein from 0.5% to 50% by weight hemihydrogenating catalyst is used relative to the total weight of the reaction mixture.

8. The process according to claim 7, wherein from 1% to 35% by weight hemihydrogenating catalyst is used relative to the total weight of the reaction mixture.

9. The process according to claim 1, wherein the hemihydrogenating is carried out at a temperature of less than or equal to 150° C.

10. The process according to claim 9, wherein the hemihydrogenating is carried out at a temperature of less than or equal to 120° C.

11. The process according to claim 10, wherein the hemihydrogenating is carried out at a temperature of less than or equal to 100° C.

12. The process according to claim 1, wherein the hemihydrogenating is carried out at a hydrogen pressure of between 1 bar and 100 bar.

13. The process according to claim 12, wherein the hemihydrogenating is carried out at a hydrogen pressure of between 5 bar and 50 bar.

14. The process according to claim 1, wherein the hemihydrogenating is carried out in the presence of water or a solvent and the water or solvent is removed during the distilling step.

15. The process according to claim 1, wherein said distilling is performed at less than atmospheric pressure, and after said distilling the aminonitrile contains less than or equal to 5% by weight dinitrile and less than or equal to 5% by weight of by-products containing an amine or imine functional group.

16. The process according to claim 1, wherein the distilled aminonitrile comprises an aliphatic aminonitrile of formula (II):

$$N\equiv C-R-CH_2-NH_2 \quad (II)$$

in which R denotes a linear or branched alkylene or alkenylene radical comprising from 1 to 12 carbon atoms, and wherein the cyclizing by hydrolysis occurs in the presence of a solid catalyst.

17. The process according to claim 16, wherein R comprises from 1 to 6 carbon atoms.

18. The process according to claim 16, wherein the solid catalyst is a molecular sieve.

19. The process according to claim 18, wherein the molecular sieve is an acidic zeolite, a silicalite, a nonzeolitic molecular sieve, a metal phosphate, or an acidic or amphoteric bulk oxide.

20. The process according to claim 19, wherein the molecular sieve is an acidic or amphoteric bulk oxide, and the bulk oxide is $SiO_2/Al_2O_3$, $SiO_2/Ga_2O_3$, $SiO_2/Fe_2O_3$, $SiO_2/B_2O_3$, halogenated alumina, sulphated zirconia, niobium oxide, tungsten oxide, thoria, zirconia, titanium dioxide, ceria or an alumina.

21. The process according to claim 19, wherein the molecular sieve is a metal phosphate which comprises a metal phosphate of formula (III):

$$MH_h(PO_4)_n \cdot (Imp)_p \quad (III)$$

in which:

M denotes one or more of a divalent, trivalent tetravalent or pentavalent element of group IIA, group IIIB, group IVb, group Vb, group VIb, group VIIb, group VIII, group IIb, group IIIa, group IVa, or group Va of the Periodic Classification of the elements;

Imp denotes a basic impregnating compound comprising one or more of alkali metal compounds containing counteranions and alkaline earth metal compounds containing counteranions, wherein said counteranions ensure electrical neutrality;

n denotes 1, 2, or 3;

h denotes 0, 1 or 2; and p denotes a number between 0 and $\frac{1}{3}$ and corresponds to a molar ratio of the impregnating compound Imp to the impregnated $MH_h(PO_4)_n$.

22. The process according to claim 19, wherein the molecular sieve is a metal phosphate which comprises a metal phosphate of formula (III):

$$O=MH_h(PO_4)_n \cdot (Imp)_p \quad (III)$$

in which:

M denotes a pentavalent element;

Imp denotes a basic impregnating compound comprising one or more of alkali metal compounds containing counteranions and alkaline earth metal compounds containing counteranions, wherein said counteranions ensure electrical neutrality;

n denotes 1, 2, or 3;

h denotes 0, 1 or 2; and p denotes a number between 0 and $\frac{1}{3}$ and corresponds to a molar ratio of the impregnating compound Imp to the impregnated $MH_h(PO_4)_n$.

23. The process according to claim 20, wherein the bulk oxide is an alumina.

24. The process according to claim 23, wherein the alumina is an activated alumina with a specific surface area of 5 m²/g to 500 m²/g.

25. The process according to claim 24, wherein the activated alumina has a specific surface area of 10 m²/g to 500 m²/g.

26. The process according to claim 1, wherein the molar ratio of the water to the distilled aminonitrile is between 0.5 and 50.

27. The process according to claim 23, wherein the molar ratio of the water to the distilled aminonitrile is between 1 and 20.

28. The process according to claim 24, wherein the molar ratio of the water to the distilled aminonitrile is between 2 and 20.

29. The process according to claim 1, wherein the hydrolyzing is carried out at a temperature between 200° C. and 400° C.

30. The process according to claim 29, wherein the hydrolyzing is carried out at a temperature between 250° C. and 400° C.

31. A process for the preparation of a lactam comprising:

hemihydrogenating an aliphatic dinitrile in the presence of a catalyst to form an aminonitrile containing unreacted aliphatic dinitrile and by-products containing an imine or amine functional group;

distilling the aminonitrile, wherein the aminonitrile contains unreacted aliphatic dinitrile and by-products containing an amine or imine functional group; and hydrolyzing the distilled aminonitrile with water in the vapor phase in the presence or the absence of a catalyst to form said lactam.

* * * * *